(12) United States Patent
Heid et al.

(10) Patent No.: US 7,210,306 B2
(45) Date of Patent: May 1, 2007

(54) TEMPERING DEVICE FOR A MICROTOME

(75) Inventors: Hans L. Heid, Bammental (DE); Dieter Teppke, Schwetzingen (DE); Reiner Fank, Rauenberg (DE); Manfred Berleth, Eppelheim (DE)

(73) Assignee: Microm International GmbH, Walldorf (DE)

( * ) Notice: Subject to any disclaimer, the term of this patent is extended or adjusted under 35 U.S.C. 154(b) by 137 days.

(21) Appl. No.: 10/527,750

(22) PCT Filed: Sep. 5, 2003

(86) PCT No.: PCT/EP03/09856

§ 371 (c)(1),
(2), (4) Date: Mar. 14, 2005

(87) PCT Pub. No.: WO2004/029588

PCT Pub. Date: Apr. 8, 2004

(65) Prior Publication Data

US 2006/0005562 A1 Jan. 12, 2006

(30) Foreign Application Priority Data

Sep. 21, 2002 (DE) ................................ 102 44 055

(51) Int. Cl.
*F25D 23/12* (2006.01)
(52) U.S. Cl. ........................................ 62/320; 83/915.5
(58) Field of Classification Search ................... 62/293, 62/320; 83/915.5
See application file for complete search history.

(56) References Cited

U.S. PATENT DOCUMENTS 3,236,133 A * 2/1966 De Pas ........................ 83/170
3,296,821 A 1/1967 Malinin

FOREIGN PATENT DOCUMENTS

| DE | 19 62 263 | 6/1967 |
|---|---|---|
| DE | 195 28 180 | 2/1997 |
| DE | 196 40 044 | 4/1998 |
| DE | 202 14 646 | 11/2002 |

* cited by examiner

*Primary Examiner*—William E. Tapolcai
(74) *Attorney, Agent, or Firm*—Dr. Paul Vincent

(57) ABSTRACT

The invention relates to a tempering device (1) for objects (2) located on the object carrier (3) of a microtome (4) of a cryostat (5) comprising an operating means supply (6) connected to a cooling device or a cooling and heating device (7) arranged on the object carrier (3), and a temperature control system. According to the invention, one such tempering device (1) is embodied in such a way that the operating means supply (6) does not hinder the work carried out on the microtome (4), and the accuracy of the cut is affected as little as possible. To this end, the operating means supply (6) is displaceably positioned in a guiding element (12) which is arranged on the guiding carriage (8) for the advancing movement (9) and the cutting movement (10) of the object head (11) and is oriented parallel to the direction of advancement (9), in such a way that it can be guided away from the object head (11).

14 Claims, 1 Drawing Sheet

TEMPERING DEVICE FOR A MICROTOME

This application is the national stage of PCT/EP2003/009856 filed on Sep. 5, 2003 and claims Paris Convention priority of DE 102 44 055.7 filed Sep. 21, 2002.

BACKGROUND OF THE INVENTION

The invention concerns a tempering device for objects on the object carrier of a microtome in a cryostat, with an operating means supply connected to a cooling means or to a cooling and heating means disposed on the object carrier, and with a temperature control.

Tempering devices of this type permit cutting of frozen histological samples in a cryostat at different temperatures without having to change the temperature of the cryostat chamber. Different tissue types such as e.g. fat or brain can be optimally cut at different temperatures e.g. in the region between −30 and −35° or from −15°. Bringing the temperature of the entire cryostat chamber to the desired temperature would require a substantial amount of time. For this reason, the leaflet "Universal-Mikrotom-Kryostate Serie HM 500" offers an equipment variant "O" which is representative of the above-mentioned conventional tempering device. The cryostat chamber is thereby at an average temperature and the tempering device provides the desired object temperature.

In this tempering device, the operating means supply is directly guided away from the cooling means or the cooling and heating means disposed on the object carrier, laterally held by a bracket, and guided as a cable and tube bundle to the inner wall of the cryostat chamber. This arrangement is disadvantageous in that this operating means supply impedes work on the microtome, since it requires an excessive amount of space in that region where work has to be carried out on the microtome, such as sample and knife exchange. Moreover, this operating means supply exerts a force onto the object carrier due to its lateral arrangement, in view of its weight and the rigidity caused by the cold.

Such a one-sided force acting directly on the object carrier influences the cutting accuracy which must be in the p range for very fine sections.

A tempering device of the above-mentioned type with lateral path guidance of the operating means supply from the object carrier is also described in DE 196 40 044 A1. DE 19 62 263 U1 discloses a tempering device, from which the operating means supply is guided away from the object carrier in a manner which is not described in detail.

DE 195 28 180 C2 also discloses a power supply for a measuring amplifier used with means for detecting advance of the object head. This measuring element, however, is disposed downstream of the object head in an insulating body which is rigidly borne in a hollow cylinder serving as an object head carrier. The power supply exits the hollow cylinder and the lower side of the cylinder guidance in the form of a freely suspended cable harness, wherein the respective openings are dimensioned to prevent the cable from being clamped during the adjusting motions.

This document provides no suggestion for designing an operating means supply of a tempering device. A tempering device of this type must be located directly on the object carrier to be able to cool the object. If the operating means supply of a tempering device of the above-mentioned type were to be disposed on the rear side of the object head carrier, similar to the above-mentioned power supply, it would have to be guided through the object head carrier and the guiding carriage. The person skilled in the art is thereby confronted with the unsolved problem of how to replace and adjust the object head. Towards this end, the operating means supply should be guided through an object carrier receptacle in a separable manner and should not impair pivoting of the object carrier (designed as an articulated ball in the above-mentioned document) in order to orient it. Consequently, an arrangement of an operating means supply for a tempering device designed in accordance with the above-mentioned electrical supply is not possible or would require unacceptable technical effort. The operating means supply must rather be guided directly away from the tempering device, thereby producing the problems which were described in connection with the tempering device of the embodiment variant "O" of the above-mentioned cryostat.

It is therefore the underlying purpose of the invention to provide a tempering device of the above-mentioned type which does not impair work on the microtome and minimally impairs the cutting accuracy.

SUMMARY OF THE INVENTION

This object is achieved in accordance with the invention in that the operating means supply is displaceably positioned in a guidance which is arranged on the guiding carriage for the supply and cutting movement of the object head and is oriented parallel to the supply direction in such a way that it can be guided away from the object head.

With the inventive arrangement, the operating means supply is not guided away from the cooling means or the cooling and heating means on the object head, and partially supported and partially suspended throughout the cryostat chamber, rather can be guided relatively close to the object head in the direction of the guidance carriage. Due to this geometry, it is no longer in the way when working on the microtome. Since the guiding carriage follows the cutting motion with the object head and the object, the operating means guidance exerts practically no force on the object head during the cutting motion such that the accuracy can no longer be impaired by such forces.

The relative motion required between the object head and the guiding carriage, is the supply motion performed before each step. This supply motion is taken into consideration in that the operating means supply is displaceably disposed in the guidance and can be displaced in accordance with the supply. The guidance must thereby be designed such that the operating means supply smoothly runs therein but is still held such that further guidance of the operating means supply after the guiding carriage cannot produce any considerable tensile forces through the guidance to the object head. The latter is therefore free from forces which could impair accuracy. If the forces of the further advanced operating means guidance act on the guiding carriage instead of the object head, in a region remote from the object head, these forces do not impair the cutting accuracy, since the point of action of such forces is far away from the cutting region and no longer at the side thereof.

In a useful embodiment, the operating means supply is guided away from the lower side of the cooling means or the cooling and heating means. It thereby extends in a region where it does not impair work on the object head of the microtome or knife carrier. The operating means supply is designed such that it supplies the required operating means to the cooling or the cooling and heating means. Usually, liquid supply, liquid discharge and at least one cable connection are required, wherein the latter controls the temperature. Electricity may also constitute an operating means.

To obtain an easy, preferably play-free guidance, which also accepts the tensile forces caused by further passage of the operating means supply to the inner wall of the cryostat, the guidance preferably consists of at least one tube which is supported by three line guides. The operating means supply may thereby be effected via a tube or via three separate supplies, one for liquid supply, one for liquid discharge, and one for the at least one cable connection. If the tube is made from metal and the line guides are formed from a plastic material, a low-wear easy running and play-free bearing is obtained which is minimally impaired through shrinking and expansion of the material due to the large temperature differences.

Since the object carrier must often be oriented through pivoting same relative to the guiding carriage, the operating means supply preferably comprises at least one elastic arc between the cooling or the cooling and heating means and the guidance, which permits such fluctuations. If the object carrier is oriented in this manner, the operating means supply is also displaced which is facilitated by the fact that it is displaceably disposed in the guidance.

To accommodate the space requirements, the arrangement is in areas which require no permanent work, and with regard to the acting forces, the operating means supply leaves the guidance on the rear side of the guiding carriage and is guided through at least one large elastic arc to a holder on the inner wall of the cryostat. During the cutting motion performed by the guiding carriage with the object head, only small tensile forces are produced which do not impair the cutting quality since their point of action is distant from the cutting area.

Since the microtome must be removed from the cryostat chamber to perform different work on the microtome, at least one coupling is suitably provided for separating the operating means supply portion which is disposed in the cryostat chamber. In this manner, the coupling can be released, the microtome can be removed from the cryostat chamber and it can be brought into the cooling chamber and connected after performance of the intended work.

The cooling means or cooling and heating means can have different designs. An evaporator may e.g. be provided as a pure cooling means, in which a cooling liquid is evaporated thereby reducing the object temperature to a desired value. In another possibility, a heat exchanger is provided which can be operated as a cooling and also as a heating means depending on whether the liquid guided therein is colder or warmer than the temperature of the cryostat chamber.

The cooling means or cooling and heating means may comprise at least one Peltier element which facilitates generation of heat or cold on the plate of the Peltier element facing the object, through pole reversal of the current connection. In a particularly favorable design, the Peltier element serves to discharge heat or cold to the object carrier and the heat exchanger serves to discharge heat from the Peltier element, if the latter is used to cool the object. In this manner, the simple temperature control of the Peltier element is utilized to assure that the generation of heat by the Peltier element associated with generation of cold for the object does not heat the cryostat chamber. This would otherwise have to be compensated for by the cryostat cooling means which would be disadvantageous in view of the energy balance and control accuracy.

A pure cooling means or a cooling and heating means may of course be designed in another manner. The operating means supply and the nature of its detailed design, depend on the precise embodiment. Irrespective thereof, the invention guarantees a spatially favorable arrangement which prevents forces which could influence the cutting quality.

The invention is explained below with reference to an embodiment shown in the drawing.

DESCRIPTION OF THE PREFERRED EMBODIMENT

Figure 1:
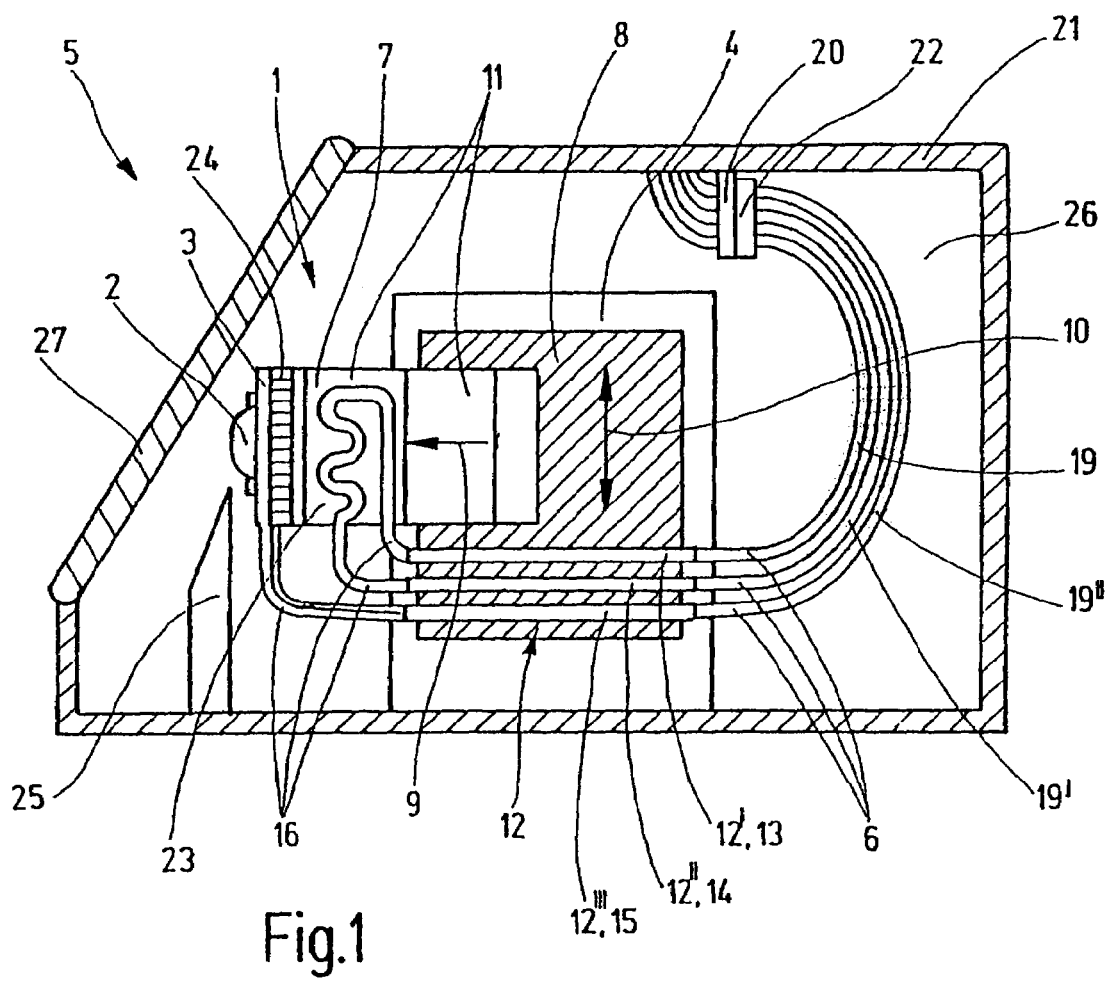
FIG. 1 shows a schematic diagram of the embodiment.

FIG. 1 shows a schematic diagram of an embodiment of the cryostat 5 with an inventive tempering device 1. For cutting objects 2, usually low-temperature histological samples, a microtome 4 is disposed in the cryostat chamber 26 of a cryostat 5. The cryostat chamber 26 is cooled to an average working temperature using a cooling means (not shown). A cooling means or a cooling and heating means 7 which is disposed on the object carrier 3 for the object 2 adjusts the optimum working temperature for cutting the object 2. An operating means supply 6 operates the cooling means or the cooling and heating means 7 by supplying it with a cooling agent and electricity.

In the embodiment shown, the object carrier 3 is disposed on a Peltier element 24 which cools or heats the object 2 depending on whether it must be cut in a temperature range above or below the cryostat chamber temperature. If the Peltier element 24 is used for cooling, a considerable amount of heat is produced on its plate facing away from the object 2 which is suitably discharged. Towards this end, a heat exchanger 23 is provided through which e.g. cold brine flows and which discharges the heat of the Peltier element 24 to prevent heating of the cryostat chamber 26.

The cooling means or cooling and heating means 7 including object carrier 3 are disposed on an object head 11 which is disposed in a guiding carriage 8 such that the object 2 can be advanced in the direction of arrow 9 by an amount corresponding to the thickness of the section for the next cut. This guiding carriage 8 is disposed in the microtome 4 such that it can exert the cutting motion shown by the double arrow 10 thereby guiding the object 2 past a knife holder with knife 25. The adjustment elements, carriage guidance and drives are not shown.

In accordance with the above-mentioned prior art, the operating means supply 6 of the cooling or the cooling and heating means 7 is laterally guided away to the inner wall 21 of the cryostat chamber 26. The invention avoids the associated disadvantages described above, in that the operating means supply 6 is directly guided from the cooling or cooling and heating means 7 to a guidance 12 which is disposed in the guiding carriage 8. Elastic arcs 16 are provided which permit the object carrier 3 on the object head 11 to be slightly pivoted to allow adjustment of the object 2 relative to the knife 25.

The guidance 12 leaves the guiding carriage 8 on the rear side and subsequently, the operating means supply 6 is guided in large elastic arcs 19, 19', 19" to a holder 20 which is disposed on the inner wall 21 of the cryostat chamber 26. This holder 20 has a coupling 22 for interrupting the operating means supply 6 of the cooling or cooling and heating means 7 and suitably also other supply lines of the microtome 4 to be able to remove the microtome 4 from the cryostat chamber 26. These lines are guided further outward by the stationary coupling half located on the holder 20 to connect them with corresponding devices and further connections (not shown). The coupling 22 may also of course be disposed at another location of the operating means supply 6 within the cryostat chamber 26.

An opening 27 in the form of a sliding or folding door is provided on the front side of the cryostat 5 which serves to supply objects 2 to the object carrier 3 or replace knifes on the knife holder 25 and which is also only schematically shown. The opening 27 also serves to remove the microtome 4 as described above to be able to perform work thereon.

Figure 2:
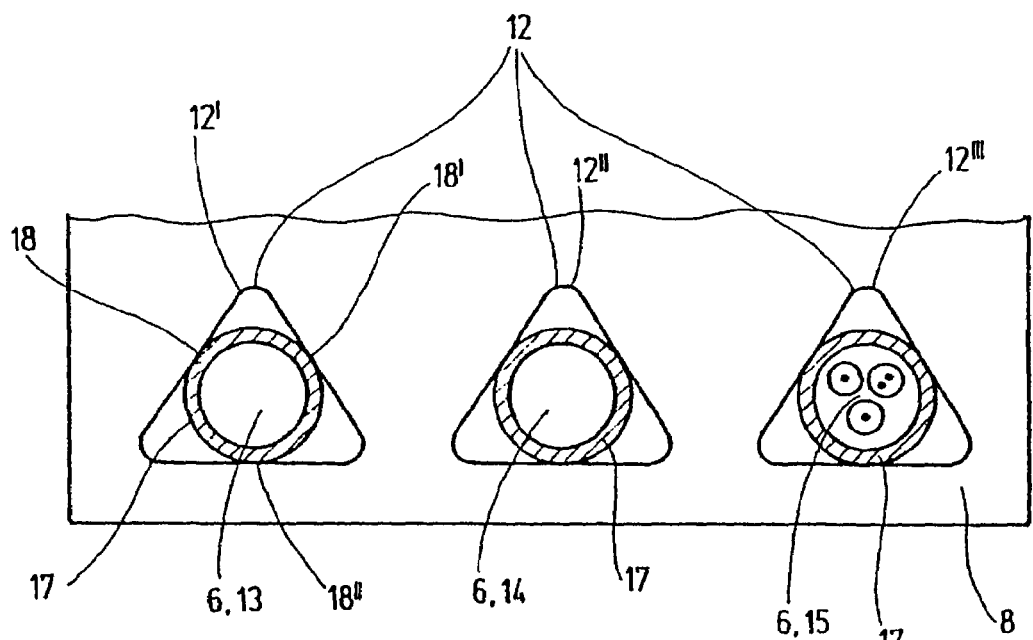
FIG. 2 shows a detail thereof.

The operating means supply 6 of FIG. 1 is explained in more detail with reference to the more detailed illustration of FIG. 2. After passage of the operating means supply 6 through the elastic arcs 16, it is connected to the guidance 12. In the embodiment shown, the guidance 12 comprises individual guidances 12', 12" and 12''', wherein liquid supply 13, liquid discharge 14 and illustrated cable connections 15 are each separately guided.

These three individual guidances 12', 12", 12''' are designed as tubes 17 in which, for the individual guidances 12' and 12", the brine is supplied to and from the cooling or cooling and heating means 7. The required cable connections 15 are disposed in the individual guidance 12'''. They are e.g. the current supply for the Peltier element 24 and also the lead of a sensor which serves as a temperature control.

One substantial feature of the guidance 12 or the individual guidances 12', 12" and 12''' is that they are guided to be smoothly running but can accept the forces which can be generated through further passage of the operating means supply 6 through large elastic arcs 19, 19', 19". The tubes 17 each have line guides 18, 18', 18". The tubes 17 are preferably made from metal and the components which contain the line guides 18, 18', 18" can be made from a plastic material which exerts a relatively small frictional force on the metal. This plastic material should also be flexible to be able to adapt to shrinking and expansion due to large temperature fluctuations. These plastic elements are accommodated in the guiding carriage 8 (not shown in detail).

This is of course only one embodiment of the inventive solution. It would also be possible to design the guidance 12 in a different manner, while observing the above-mentioned properties. The guidance 12 could e.g. be designed as a tube 17, in which the liquid supply 13 and also the liquid discharge and the cable connections 15 are disposed. Provision of a Peltier element 24 would also be feasible, wherein the operating means supply 6 merely consists of electric cable connections 15 which are guided in a corresponding manner. The further guidance of the operating means supply 6 after the guidances 12 could also be different. It is thereby merely essentially that such a further guidance permits the cutting motion shown by the double arrow 10 without any critical forces acting on the guiding carriage 8.

List of Reference Numerals
1 tempering device
2 object
3 object carrier
4 microtome
5 cryostat
6 operating means supply
7 cooling or cooling and guiding means
8 guiding carriage
9 arrow: supply
10 double arrow: cutting motion
11 object head
12 guidance
12',12",12''' individual guidances
13 liquid supply
14 liquid discharge
15 cable connection(s)
16 elastic arc
17 tube
18,18',18" line guides
19,19',19" large elastic arcs
20 holder
21 inner wall of the cryostat chamber
22 coupling
23 heat exchanger
24 Peltier element
25 knife holder with knife
26 cryostat chamber
27 opening of the cryostat chamber for microtome operation (e.g. sliding or folding door)

We claim:

1. A tempering device for slicing an object in a microtome, the device comprising:
   a cryostat;
   an object carrier disposed in said cryostat for holding the object;
   an object head cooperating with and supporting said object carrier;
   a temperature adjustment means disposed in said object head to heat or cool the object;
   a guiding carriage cooperating with said object head to advance the object prior to slicing;
   operating means supply connected to said temperature adjustment means to heat or cool the temperature adjustment means; and
   a guidance mounted on or in said guiding carriage, said guidance bearing said operating means supply in a displaceable manner, said guidance oriented substantially parallel to a direction of advance of said guidance carriage to lead said operating means supply away from said object head.

2. The tempering device of claim 1, wherein said operating means supply is guided away from a lower side of said temperature adjustment means.

3. The tempering device of claim 1, wherein said operating means supply comprises a liquid supply, a liquid discharge, and at least one cable connection.

4. The tempering device of claim 1, wherein said guidance comprises at least one tube guided via three line guides.

5. The tempering device of claim 4, wherein an inside of said at least one tube serves as said operating means supply.

6. The tempering device of claim 1, wherein said guidance comprises three individual guidances, wherein two individual guidances constitute a liquid supply and a liquid discharge and one individual guidance is for at least one cable connection.

7. The tempering device of claim 4, wherein said tube comprises metal and said line guides comprise a plastic material.

8. The tempering device of claim 1, wherein said operating means supply travels through at least one elastic arc between said temperature adjustment means and said guidance to permit orientation of said object carrier through pivoting same relative to said guiding carriage.

9. The tempering device of claim 1, wherein said operating means supply exits said guidance on a rear side of said guiding carriage and passes, through a large elastic arc, to a holder disposed on an inner wall of said cryostat.

10. The tempering device of claim 9, further comprising at least one coupling for separating a portion of said operating means supply which extends within said cryostat.

11. The tempering device of claim 1, wherein said temperature adjustment means comprises an evaporator cooler.

12. The tempering device of claim 1, wherein said temperature adjustment means comprises a heat exchanger.

13. The tempering device of claim 1, wherein said temperature adjustment means comprises at least one Peltier element.

14. The tempering device of claim 12, wherein said temperature adjustment means comprises at least one Peltier element which communicates with said object carrier to discharge heat or cold, wherein said heat exchanger communicates with said Peltier element to discharge heat.

* * * * *